United States Patent
Hutten et al.

(10) Patent No.: US 6,917,832 B2
(45) Date of Patent: Jul. 12, 2005

(54) STIMULATION APPARATUS

(75) Inventors: Helmut Hutten, Graz (AT); Max Schaldach, deceased, late of Erlangen (DE); by Max Schaldach, Jr., legal representative, Berlin (DE)

(73) Assignee: BIOTRONIK Mess- und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 405 days.

(21) Appl. No.: 10/167,987

(22) Filed: Jun. 12, 2002

(65) Prior Publication Data

US 2002/0193837 A1 Dec. 19, 2002

(30) Foreign Application Priority Data

Jun. 14, 2001 (DE) .......................................... 101 29 649

(51) Int. Cl.⁷ ................................................. A61N 1/37
(52) U.S. Cl. ......................................................... 607/28
(58) Field of Search ...................................... 607/1–72

(56) References Cited

U.S. PATENT DOCUMENTS

| | | | |
|---|---|---|---|
| 5,350,410 A | | 9/1994 | Kleks |
| 5,391,191 A | | 2/1995 | Holmstrom |
| 5,411,533 A | | 5/1995 | Dubreuil |
| 5,417,718 A | | 5/1995 | Kleks |
| 5,431,693 A | | 7/1995 | Schroeppel |
| 5,476,487 A | * | 12/1995 | Sholder ........................ 607/28 |
| 5,480,414 A | | 1/1996 | Stroebel |
| 5,674,254 A | | 10/1997 | van Krieken |
| 5,718,720 A | * | 2/1998 | Prutchi et al. ................. 607/28 |
| 6,134,471 A | * | 10/2000 | Dauer et al. ................... 607/17 |

FOREIGN PATENT DOCUMENTS

| | | |
|---|---|---|
| DE | 40 13 048 A1 | 10/1991 |
| DE | 100 46 241 A1 | 5/2001 |

* cited by examiner

*Primary Examiner*—Scott M. Getzow
(74) *Attorney, Agent, or Firm*—Hahn Loeser + Parks LLP

(57) ABSTRACT

A stimulation apparatus, in particular for a human heart, has a stimulation unit, a signal detector and a control unit. The stimulation unit is adapted to deliver a stimulation pulse having a pulse duration, a pulse strength and a stimulation intensity. The signal detector is adapted to detect stimulation success on the basis of a picked-up signal. The control unit is connected to the stimulation unit and to the signal detector. It is designed such that the stimulation intensity varies depending upon the picked-up signal. A time-determining unit is provided that is at least indirectly connected to the control unit and with which a time difference between the delivery of a stimulation pulse and the pick-up of the picked-up signal or a signal feature of the picked-up signal can be detected.

24 Claims, 3 Drawing Sheets

STIMULATION APPARATUS

The invention concerns a stimulation apparatus, in particular for a human heart, comprising a stimulation unit which is adapted to deliver a stimulation pulse having a pulse duration, a pulse strength and a stimulation intensity, a signal detector which is adapted to detect stimulation success on the basis of a picked-up signal, and a control unit which is so connected to the stimulation unit and to the signal detector and designed that the stimulation intensity is variable in dependence on the picked-up signal.

BACKGROUND OF THE ART

The specified stimulation apparatuses also include in particular implantable cardiac pacemakers. They are usually connected by way of an electrode line to an electrode arranged in a heart, and adapted to deliver electrical stimulation pulses to the heart by way of the electrode. Those stimulation pulses serve to excite the cardiac tissue or myocardium and, depending on the respective kind of pacemaker, are delivered in particular when the heart does not contract in a natural fashion. In that case contraction is caused by electrical stimulation of the cardiac tissue.

Such an electrical stimulation pulse must involve a stimulation intensity which is above a respective stimulation threshold. In that respect the stimulation threshold is a measurement in respect of the minimum stimulation intensity which is sufficient to cause dipolarisation of the myocardium and thus contraction of a respective chamber of the heart. The stimulation threshold depends on various factors and in addition it is also variable under some circumstances in the course of time.

Besides the requirement to deliver a stimulation pulse of adequate stimulation intensity, there is a need for the energy to be applied for a stimulation pulse to be kept as low as possible. That energy is usually taken from a battery of the pacemaker, which becomes exhausted in the course of time. When that battery is exhausted the pacemaker has to be replaced by a new one by means of an operation.

There is therefore on the one hand the requirement that the stimulation intensity of a stimulation pulse must be sufficient to trigger contraction of the cardiac tissue. In that respect the stimulation intensity depends on the one hand on the duration of a stimulation pulse and on the other hand on the strength of a stimulation pulse. The strength of a stimulation pulse in turn depends on the electrical voltage with which a stimulation pulse is delivered to the cardiac tissue. This means that a greater energy consumption is usually linked to a greater stimulation intensity.

On the other hand there is the need for the energy consumption per stimulation pulse to be kept as low as possible as that energy is taken from a battery of the pacemaker, which becomes exhausted in that way. When the battery of the pacemaker is exhausted an operation is required to replace the pacemaker or the battery. Therefore, a reduction in the level of energy consumption of the pacemaker entails a longer service life for the pacemaker.

There is therefore a need to satisfy the requirements for a level of stimulation intensity which is as low as possible and at the same time a stimulation effect which is regularly successful, by optimisation of the stimulation intensity. In that respect, it is known from the state of the art, for example from U.S. Pat. Nos. 5,350,410; 5,411,533; 5,431,693 and 5,674,254, after delivery of a stimulation pulse, for the stimulation outcome (capture) to be detected (capture recognition), in order to trigger a backup stimulation pulse at least in the event of defective stimulation outcome.

In comparison with the known cardiac pacemakers with capture recognition and adaptation of stimulation intensity, there is in particular the wish for a lack of stimulation success to be recognised as quickly as possible in order to be able to deliver a backup stimulation pulse as quickly as possible in relation to the previously delivered stimulation pulse.

That involves the problem of reliable and rapid stimulation outcome monitoring.

SUMMARY OF THE INVENTION

In accordance with the invention that problem is resolved by a stimulation apparatus of the kind set forth in the opening part of this specification, which has a time-determining unit which is at least indirectly connected to the control unit and with which a time difference between the delivery of a stimulation pulse and the pick-up of the picked-up signal or a signal feature of the picked-up signal can be detected.

The invention is based on the realisation that the time difference between the delivery of a stimulation pulse and the detection of stimulation success is a measurement of whether the stimulation intensity corresponds to the stimulation threshold or is markedly above same, that is to say is superthreshold. In the case of markedly superthreshold stimulation intensity, the time difference between the delivery of the stimulation pulse and detection of the stimulation success or detection of a signal feature characterising stimulation success is shorter than with a stimulation intensity which is adapted in the optimum manner. If in contrast the stimulation intensity is inadequate, possibly no stimulation success whatsoever can be detected.

Insofar as just the time between the stimulation pulse delivery and the expected stimulation outcome is used as a measurement on the one hand for determining the optimum stimulation intensity and on the other hand for monitoring the stimulation outcome, the delivery of a backup stimulation pulse can be implemented as early as possible. More specifically, it is only necessary in each case to wait for the period of time, after which the stimulation outcome is to be expected at the latest after delivery of a stimulation pulse, in order after the expiry of that time to deliver a backup pulse as quickly as possible. If in contrast the stimulation outcome occurs markedly earlier than at the expected time, the level of stimulation intensity can be reduced stepwise.

The time difference detected by the stimulation apparatus is thus ideally a measurement at the same time for adaptation of the level of stimulation intensity and also for monitoring the stimulation outcome.

The increase or reduction in stimulation intensity is preferably effected by the stimulation unit including two capacitors of different charges and being switched over to the respective other capacitor for the purposes of increasing or reducing the level of stimulation intensity. In the case of a dual-chamber pacemaker, the two capacitors can also be a respective capacitor of an atrial stimulation unit and a ventricular stimulation unit, which are suitably wired.

In accordance with a concept which is also independently patentable, there are therefore to be provided two charging capacitors of which one is charged up in the usual manner to the voltage which currently appears necessary for successful stimulation and the second is charged up permanently or only temporarily to a slightly lower voltage. Stimulation is then effected 'in a trial mode' using the lower voltage (that is to say, accessing the second charging capacitor). If stimulation with the lower voltage is not successful, stimulation is effected with the higher voltage previously used, immediately after the lack of success is detected. The term 'immediately after' means after at the latest 50 ms. At the latest after 50 ms (that period essentially includes autoshorting, but that interval can be still further reduced, and in principle fractal electrodes make it possible to detect the success or failure of stimulation even earlier) success of the stimulation effect can be detected by the occurrence of an evoked potential (ventricular or atrial). In the case of subthreshold stimulation (stimulation failure) therefore, no heart action is actually stopped but only the current RR-interval is prolonged by 50 ms.

Whether the second charging capacitor is permanently charged or is only temporarily charged up prior to the respective use thereof depends on which option is better in terms of the overall battery loading (that is to say leakage current, but also expenditure in terms of control electronics etc). In principle both variants are possible. In that case the control unit is designed in such a way that at the second stimulus all suitable measures such as blanking and so forth are also again implemented, that is to say the second stimulation process is in that respect a normal stimulation process which however is triggered off by the lack of success with the first process.

If the second charging capacitor is kept permanently charged up, more specifically at a voltage which is relatively slightly lower than the voltage currently used for stimulation with the first charging capacitor, then it is also possible to react rapidly thereto if the voltage currently used for stimulation becomes subthreshold due to a rise in the stimulation threshold (as typically occurs in the first weeks after electrode implantation). Detection of the subthreshold stimulation is effected as described hereinbefore within at most 50 ms after the non-occurrence of the evoked potential. In that case, the second charging capacitor which in fact is in any case already markedly charged up is charged up to a voltage which is above the charging voltage of the first capacitor, which has now become subthreshold but which was previously superthreshold. That post-charging process can be carried out much more quickly than complete recharging of the first capacitor, that is to say once again it is not an approximately complete RR-interval that is lost, but only parts thereof, before successful post-stimulation occurs.

A number of alternatives fall to be considered as criteria in regard to the reduction in stimulation voltage, that is to say for example switching over to the second charging capacitor.

One of those alternatives is switching over, as already referred to hereinbefore, on the basis of determining time, in which the stimulation success achieved with the first electrode (the actual stimulation electrode) is detected with a second electrode (which is preferably used only for sensing purposes), and then analysed. It is known that stimulation is successful only when the stimulation strength is above the threshold value in the excitable tissue outside the fibrotic capsule which surrounds the stimulation electrode and which grows with time after implantation. If now the stimulation strength not only reaches that threshold value at the edge of the fibrotic capsule but also extends markedly into the excitable tissue outside the fibrotic capsule, then the distance that the excitation must cover to reach the sensing electrode is shorter, that is to say that excitation is detected by the sensing electrode earlier than an excitation effect which is triggered by virtue of the threshold stimulation strength having only just reached beyond the edge of a fibrotic capsule which forms around an implanted electrode. That is based on the realisation that the speed of propagation of the electrical field, starting from the stimulation electrode, is markedly greater than the speed of propagation of the excitation effect. In that respect excitation basically always starts from that edge zone in which the threshold stimulation strength is just reached. It will be appreciated that, when using a second electrode (as the sensing electrode), it can also be quite definitely used to detect success or failure of stimulation.

Alternatively or additionally to the above-described time criterion, it is also possible to provide for 'blind' switching over, after a predetermined number of successful stimulation procedures at a first, superthreshold stimulation intensity. The control unit is then so designed that, after a predetermined number of successful stimulation procedures, the system switches over to a lower stimulation intensity, in particular to the second charging capacitor. Such a number can be for example 1000. The control unit preferably includes a counter for the number of successive successful stimulation procedures, which counter is reset in the case of stimulation failure or when switching over to a lower level of stimulation intensity.

If the stimulation unit includes two charging capacitors, the system is switched over to the second charging capacitor for example after every 1000 successful stimuli and, in the case of successful stimulation, its charging voltage is maintained, whereby the second charging capacitor becomes the first and the previous first takes over the function of the second, that is to say it is now charged up to a lower voltage than the new first charging capacitor (insofar as both charging capacitors are to be deemed equivalent, that is to say which is the first charging capacitor depends on the respectively current conditions involved). In turn after 1000 successful stimulation procedures there is a renewed drop in the stimulation voltage. In the event of stimulation being unsuccessful, the system is switched back to the first charging capacitor after at the latest 50 ms. At the same time, after an unsuccessful drop in the stimulation voltage, the number of 1000 to the next 'blind' attempt is increased, for example to 5000, in order to prevent frequent unsuccessful stimulation.

A further criterion for switching over the level of stimulation intensity, which is also to be applied independently, is switching over on the basis of given features in the morphology of the evoked potentials (ventricular or atrial), which indicate that the current stimulation strength (that is to say the stimulation or charge voltage of the first charging capacitor) is markedly above the stimulation threshold. Such features in the signal morphology can be given amplitude values (for example maximum values or values which can be identified by a marked change in the morphology or in the signal character), moments in time for the occurrence of given amplitude values or moments of higher order, for example gradients in the signal configuration which can be obtained by differentiation, or integrals between predetermined primary features (that is to say between amplitude values or the moment in time of the occurrence thereof), or the relationship of two selected amplitude values. Detecting such changes in the signal morphology should preferably relate to a pattern complex of the (individual) signal in question, which is obtained by averaging (for example obtained over 100 individual signals, possibly with weighting in regard to the moment in time of the occurrence prior to the respectively current individual signal). Whether there is a deviation which is sufficient in the sense of a reduction in the charging voltage for the first capacitor is preferably predetermined by a threshold value. That threshold value can relate as a percentage to the mean value of the same signal value, for example a change by 10%, or to the continuously detected standard deviation (for example when the single or double standard deviation is exceeded), or a relative value, for example the relationship of the standard deviation to the mean value.

Advantageously the stimulation apparatus is adapted to increase the level of stimulation intensity either by prolonging the pulse duration or by increasing the pulse strength or on the other hand to implement a reduction in the stimulation intensity by reducing the stimulation intensity or by shortening the pulse duration. That can be effected by the above-described procedure involving switching over between two capacitors.

In an alternative embodiment, there is provided a common electrode for delivery of the stimulation pulse and for picking up the signal to be picked up for monitoring stimulation outcome. In that case the electrode is connected both to the stimulation unit and also to the signal detector.

A preferred alternative embodiment has two separate electrodes for delivery of the stimulation pulse and for picking up the signal. The sensing electrode provided for picking up the signal is then connected to the signal detector while the electrode provided for delivery of the stimulation pulse is connected to the stimulation unit.

As already discussed hereinbefore, the stimulation apparatus is preferably adapted to reduce the stimulation intensity if the time difference between delivery of the stimulation pulse and detection of stimulation success is shorter than a stored reference value.

In addition to or as an alternative to that variant of the stimulation intensity variation, it is also possible to provide a morphology detector which is connected to the signal detector and the control unit and which is adapted to detect morphological features of the picked-up signal and to deliver a morphology signal to the control unit when predetermined morphological features occur. That morphology signal can serve on the one hand to permit the recognition of given signal features in the manner of a filter, in order in that way to permit the time difference between the delivery of the stimulation pulse and the occurrence of the signal feature. On the other hand a possibly additional signal for the variation in stimulation intensity can be derived from the signal morphology itself.

Advantageously, the stimulation apparatus is adapted to trigger a second stimulation pulse of greater stimulation intensity as a backup pulse if no stimulation success is detected after the expiry of a predetermined time after delivery of a first stimulation pulse.

In a particularly preferred variant the stimulation apparatus is adapted to independently determine the reference value for the time difference or the predetermined morphological features, by autocalibration. Variants in respect of advantageous configurations of the corresponding autocalibration unit are set forth in the appendant claims.

Finally the stimulation apparatus is preferably in the form of a cardiac pacemaker.

Further advantageous configurations are to be found in particular in the specific description hereinafter.

BRIEF DESCRIPTION OF THE DRAWINGS

The invention will be better understood when reference is made to the appended drawings, in which identical parts are identified by identical part numbers and in which.

DETAILED DESCRIPTION OF THE PREFERRED EMBODIMENT

Figure 1A:
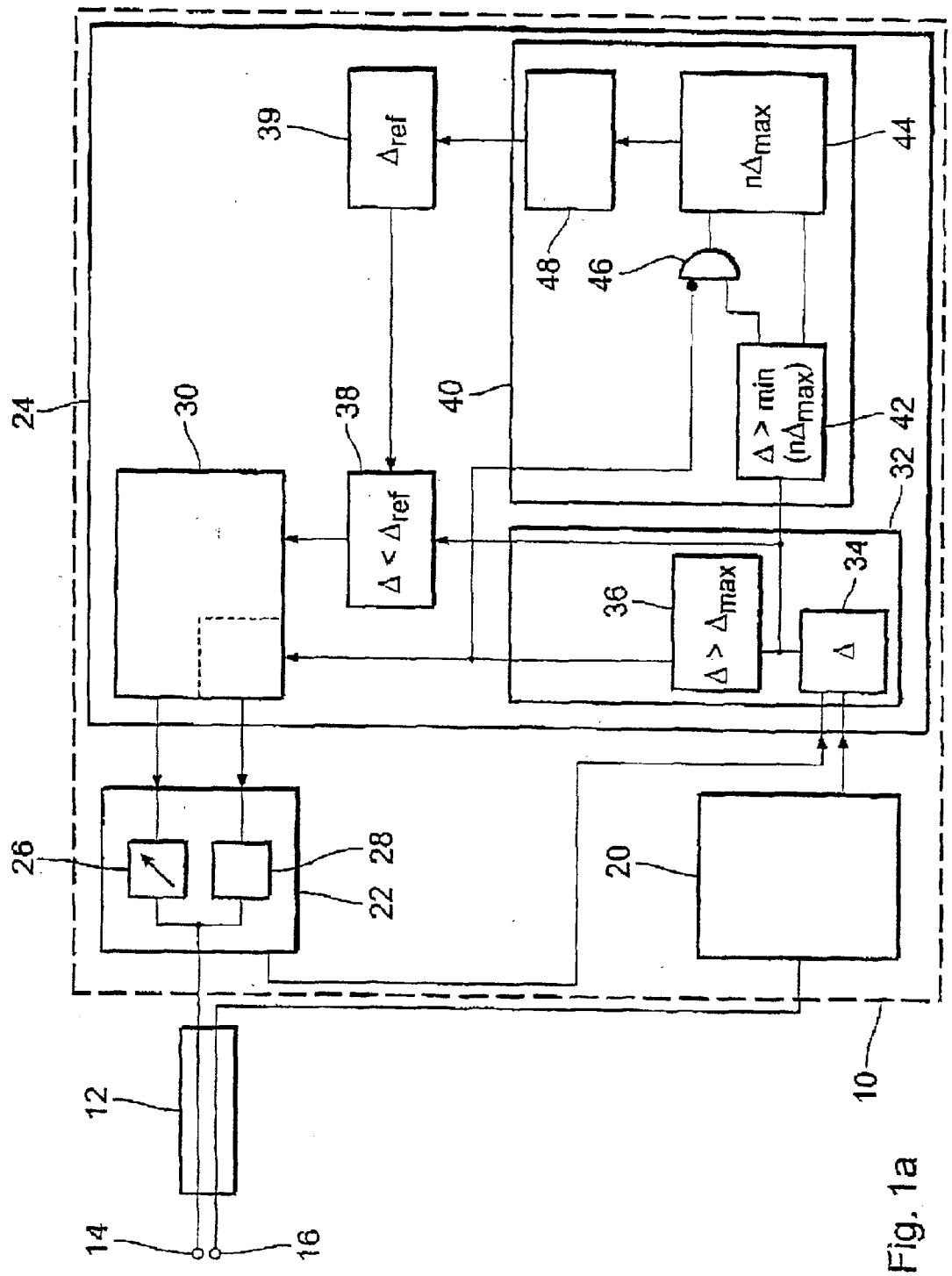
FIGS. 1a and 1b show a first variant of a stimulation apparatus with a time difference-controlled stimulation unit, in two sub-variants.

FIG. 1 shows a stimulation apparatus in the form of a cardiac pacemaker 10. The pacemaker 10 is connected by way of an electrode catheter 12 to a stimulation electrode 14 and a sensing electrode 16.

The pacemaker 10 includes a stimulation unit 22, a signal detector 20 and a control unit 24.

The signal detector 20 is connected on its input side to the sensing electrode 16. The signal detector 20 is adapted to deliver a signal at its output side when a signal is picked up by way of the sensing electrode 16, in particular when the signal detector 20 detects a given feature in a signal which is picked up by the sensing electrode 16. That feature can be for example the first rising signal edge of the signal which is picked up. The last-mentioned mode of operation permits signal detection which is as fast as possible.

The stimulation unit 22 is connected on its output side on the one hand to the stimulation electrode 14. The stimulation unit 22 includes two pulse generators, a controllable pulse generator 26 and a backup pulse generator 28. The two pulse generators 26 and 28 are connected to the stimulation electrode 14 and are adapted to deliver an electrical stimulation pulse to the stimulation electrode 14.

The controllable pulse generator 26 includes a capacitor whose charge can be varied in dependence on a variable control signal. In specific terms, the capacitor of the controllable pulse generator 26 is charged up to a voltage which is to be predetermined by the variable control signal. The backup pulse generator 28 includes a capacitor which is always charged up to a fixed voltage value. The controllable pulse generator 26 is capable of delivering a stimulation pulse which can be varied in terms of stimulation intensity. A variation in the stimulation pulse in respect of stimulation strength is possible by way of a variation in the charging voltage of the capacitor of the controllable pulse generator 26. Furthermore, the stimulation intensity can also be additionally or alternatively varied by the pulse duration of the stimulation pulse delivered by the controllable pulse generator 26 being varied. A suitable pulse duration timer is then designed to be suitably adjustable by way of a variable control signal. The stimulation intensity of the stimulation pulse delivered by the controllable pulse generator 26 is just so adjusted in each case that the stimulation intensity is sufficient to stimulate the heart, in particular the ventricle or the atrium, of a patient, at the same time with the minimum possible energy expenditure and the surest possible stimulation success. The control unit 24 is therefore adapted to regularly actuate the controllable pulse generator 26.

It is only if no stimulation success is detected by means of the control unit 24 in conjunction with the signal detector 20, after delivery of a stimulation pulse by way of the controllable pulse generator 26, that the control unit 24 triggers the backup pulse generator 28. The latter is so designed that the stimulation pulse delivered by the backup pulse generator 28 involves a stimulation intensity which is certain to be above the stimulation threshold of the cardiac tissue to be stimulated. The capacitor of the backup pulse generator 28 is therefore regularly charged to a suitably high level.

For the purposes of actuating the stimulation unit 22, the control unit 24 includes a stimulation actuation unit 30 which at the output side, for actuating the stimulation unit 22, is connected both to the controllable pulse generator 26 and also to the backup pulse generator 28.

The control unit 24 also includes a time-determining unit 32 which is connected on its input side both to the signal detector 20 and also to the stimulation unit 22. In that way the time-determining unit 32 receives a signal from the stimulation unit 22 as soon as the stimulation unit 22 outputs a stimulation pulse. The time-determining unit 32 receives a signal from the signal detector 20 when the signal detector 20 detects a picked-up signal or a feature of a picked-up signal.

The time difference between the delivery of a stimulation pulse and the occurrence of a picked-up signal or a signal feature is determined by way of a difference value-forming means 34 of the time-determining unit 32. A signal corresponding to that time difference is outputted to a difference value timer 36 of the time-determining unit 32. The difference value timer 36 determines whether the time difference between the stimulation pulse and the detected signal feature is above a predetermined maximum value. If that maximum value is exceeded a signal is delivered without delay to the stimulation actuation unit 30 which thereupon directly actuates the backup pulse generator 28. That ensures that a backup stimulation pulse is delivered if a controlled stimulation pulse which had been previously delivered has not resulted in stimulation success.

Figure 1B:
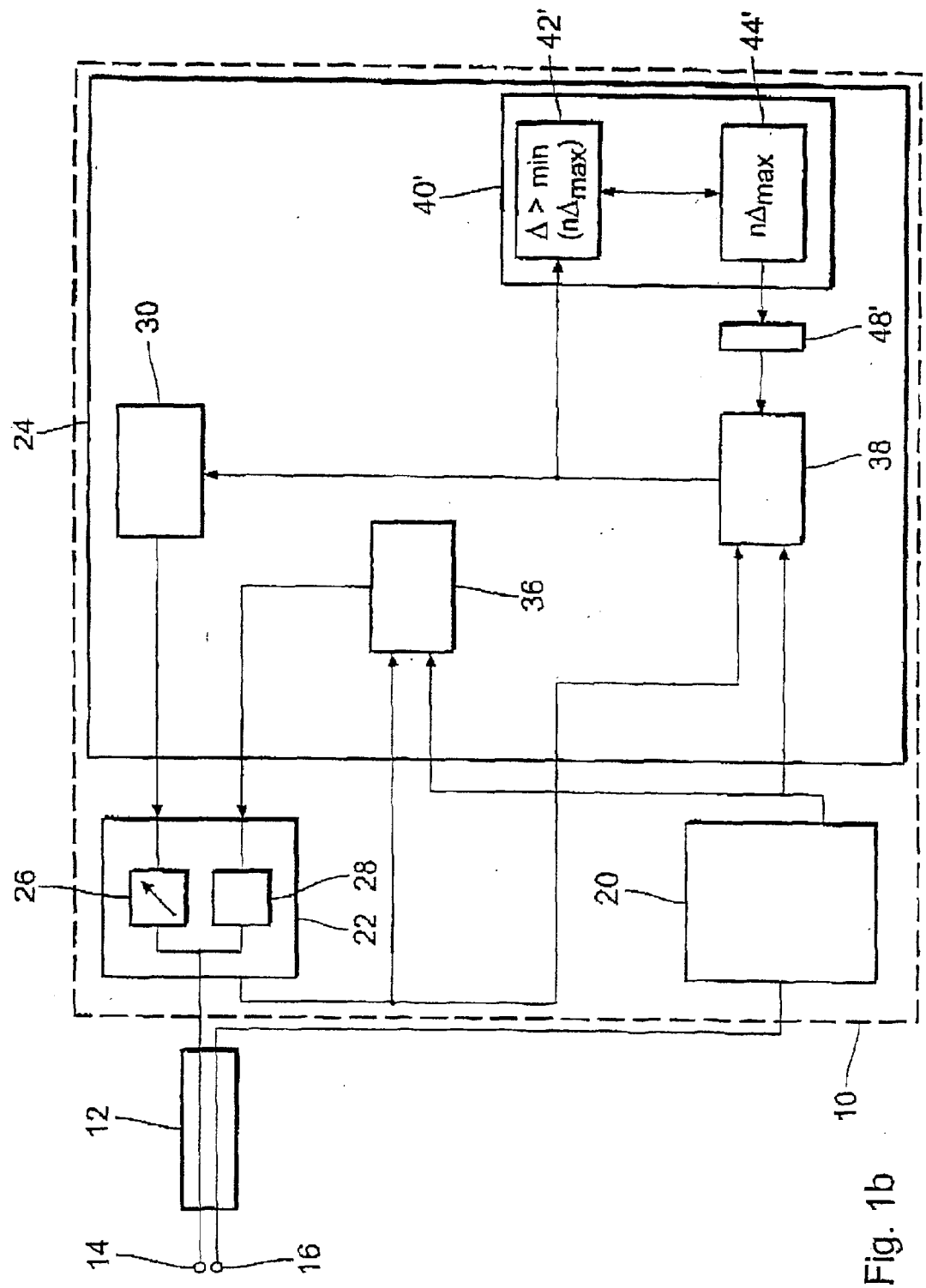

Instead of the configuration illustrated in FIG. 1a in which the signals are fed from the stimulation unit 22 and the signal detector 20 to the difference value-forming means 34 and only then to the difference value timer 36, the difference value timer 36 can also be connected directly to the stimulation unit 22 and the signal detector 20, and actually be in the form of a timer. In that case which is shown in FIG. 1b, the difference value timer is started by a signal outputted by the stimulation unit 22 simultaneously with the delivery of a stimulation pulse, and is reset by a signal from the signal detector 20. If the difference value timer 36' is not reset prior to the expiry of a predetermined time by a signal coming from the signal detector 20, the difference value timer 36', with the expiry of the predetermined time, directly outputs a signal which results in triggering of the backup pulse generator 28. For that purpose the difference value timer 36' can also be connected on the output side directly to the backup pulse generator 28.

For the purposes of controlling the stimulation intensity of regular, controlled stimulation pulses which are delivered by the controllable pulse generator 26, the control unit 24 includes a reference time difference unit 38 which in an alternative embodiment (FIG. 1a) is connected to the difference value-forming means 34 and receives a time signal corresponding to the time difference between delivery of a stimulation pulse by the stimulation unit 22 and detection of a signal feature by the signal detector 20. In the reference time difference unit 38, that time difference is compared to a reference value and a signal serving to reduce the level of stimulation intensity is delivered to the stimulation actuation unit 30 if the time difference is smaller than the reference value or the time difference is smaller by a predetermined minimum amount than the reference value. The reference value is stored in a reference value memory 39.

In an alternative design configuration (FIG. 1b) the reference time difference unit 38' can also be in the form of a timer which on the input side can be connected directly to the stimulation unit 22 for receiving a signal upon delivery of a stimulation pulse and the signal detector 20 for delivery of a signal upon the detection of predetermined signal features. The reference time difference unit 38 which is in the form of a timer is started in this embodiment just like the difference value timer 36' by a signal from the stimulation unit 22 and reset by a signal from the signal detector 20. The difference between the reference time difference unit 38' and the difference value timer 36' in this case is on the one hand that the running time, predetermined by the reference value, of the reference time of the reference time difference unit 38 is variable, while the difference value timer 36' expires after a fixedly predetermined running time. In addition the running time of the difference value timer 36' is greater than the running time of the reference time difference unit 38'.

The reference time difference unit 38' outputs a signal corresponding to the deviation in the time difference between the delivery of a stimulation pulse and detection of a stimulation success from the reference value, which signal by way of the stimulation actuation unit 30 produces the variation in the controllable pulse generator 26. In the variant in which the reference time of the reference time difference unit 38 is in the form of a timer, the deviation in the time difference between stimulation and stimulation success from the reference value arises out of the remaining running time of that timer between resetting of the timer by the signal detector 20 and expiry of the timer after the time which is predetermined by the reference value.

When the timer of the reference time difference unit 38 is reset before it expires after the time predetermined by the reference value, the controllable pulse generator 26 is actuated in such a way that the stimulation intensity of the next stimulation pulse is reduced by a value corresponding to the deviation between the time difference and the reference value. If the time difference is no smaller than the reference value, and if therefore the timer of the reference time difference unit 38 is not reset prior to expiry after a time determined by the reference value, by a signal from the signal detector 20, there is no change in the controllable pulse generator 26, in regard to a modified stimulation intensity. It can even be provided that the level of stimulation intensity is increased in the last-mentioned case.

As described hereinbefore, the change in stimulation intensity can be effected by varying the pulse duration, that is to say by adjusting a corresponding timer of the controllable pulse generator 26, or varying the stimulation strength, that is to say varying the charging voltage of the capacitor of the controllable pulse generator 26, or by means of both measures.

The control unit 24 is provided with an autocalibration unit 40, by way of which the control unit 24 is capable of independently determining the value in the reference value memory. The autocalibration unit 40 is adapted to form a suitable reference value. In the embodiment shown in FIG. 1a, for that purpose the autocalibration unit 40 includes a difference value comparison unit 42 which is connected on its input side on the one hand to the difference value-forming means 34 and on the other hand to a difference value memory 44. A predetermined number of the longest, respectively ascertained time differences is stored in the difference value memory 44. The difference value comparison unit compares a respective current time difference to one of the time differences stored in the difference value memory 44, and determines whether the respectively current time difference is greater than the smallest of the time differences stored in the difference value memory 44. If that is the case, the shortest of the time differences stored in the difference value memory 44 is replaced by the respectively current time difference. That storage of the respectively current time difference is prevented by an AND-member 46 only when the current time difference is greater than the maximum value which is predetermined for the difference value timer 36, that is to say if the difference value timer 36 delivers an output signal. That output signal is applied to an inverted input of the AND-gate 46 and thus prevents storage of the respectively current time difference. The autocalibration unit 40 further includes an averaging means 48 which is connected to the difference value memory 44 and which forms the mean value of the time differences stored in the reference value memory 44, as soon as the time differences stored in the difference value memory 44 are changed. On the output side the averaging means passes the mean value of the time differences stored in the difference value memory 44, as a reference value, into the reference value memory 39. As described above, the reference value memory 39 is connected to the reference time difference unit 38.

In the alternative configuration shown in FIG. 1b, the reference time difference unit 38 is in the form of a timer and, as described hereinbefore, determines the residual time which remains between resetting of the timer and the running time of the timer, or the time elapsing after expiry of the time determined by the reference value, until the signal is received at the signal detector 20. In that way, at the output of the reference time difference unit 38 there is a time signal with sign, which is compared in a difference value comparison unit 42' to a number of difference values stored in a difference value memory 44'. Having regard to the sign of the time signal which is determined in that way, the system determines whether the current time difference signal is greater than the smallest time difference signal value in the difference value memory 44' and possibly replaces the smallest time difference signal value by the current time difference signal value. Upon a change in the values stored in the difference value memory 44', an averaging means 48' connected to the difference value memory 44' adds those values in each case to the reference value which at the same time is the running time of the reference time difference unit 38 which is in the form of the timer. That affords as many time values as there are time signal difference values stored in the reference value memory 44'. Those time differences are averaged and afford the respectively current reference value.

Figure 2:
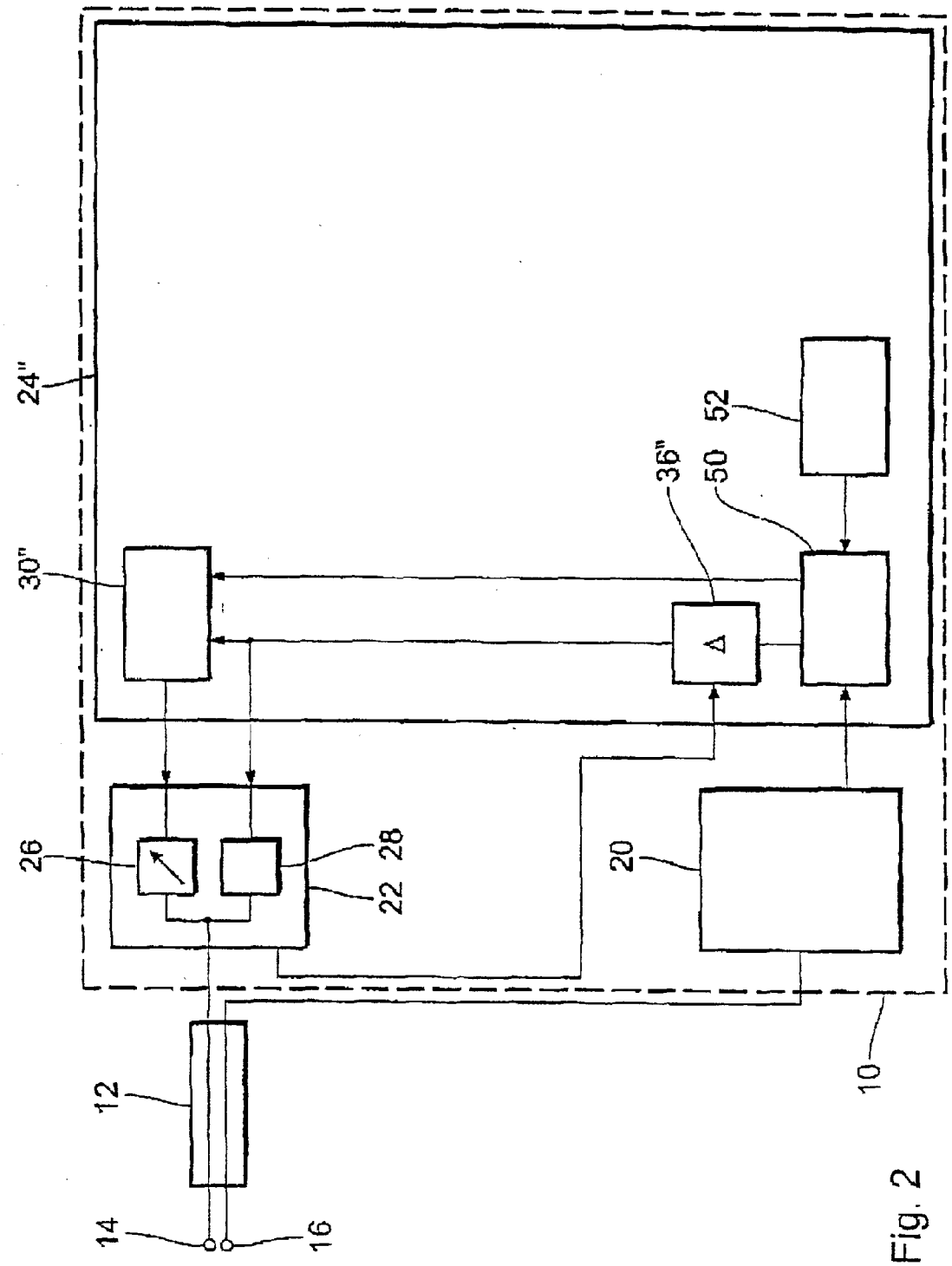
FIG. 2 shows a second variant of the stimulation apparatus with signal morphology-controlled stimulation intensity.

FIG. 2 shows an alternative pacemaker 10. Its electrode catheter 12 with stimulation electrode 14 and sensing electrode 16, as well as its signal detector 20 and its stimulation unit 22 with a controllable pulse generator 26 and a backup pulse generator 28 are identical or similar to those in the pacemakers shown in FIGS. 1a and 1b.

An alternative control unit 24" includes in particular a signal pattern comparison unit 50 which is connected on the one hand to the signal detector 20 and on the other hand to a signal pattern memory 52. The signal pattern comparison unit 50 is adapted to compare signal portions coming from the signal detector 20 of a picked-up signal to signal patterns which are stored in the signal pattern memory 52.

By virtue of that pattern comparison procedure, the signal pattern comparison unit 50 forms on the one hand a time signal which is outputted by way of a control line to a difference value timer 36". The difference value timer 36", as in the embodiment shown in FIG. 1b, is connected to the stimulation unit 22 and receives therefrom a stimulation time signal characterising the moment in time of delivery of a stimulation pulse. Formed in the difference value timer 36" is a difference time signal which comes from the time difference between the delivery of a stimulation pulse by way of the stimulation unit 22 and the detection of a signal feature by the signal pattern comparison unit 50. The last-mentioned moment in time is determined by the time signal which the signal pattern comparison unit 50 delivers to the difference value timer 36". The difference time signal is outputted from the difference value timer 36" by way of a signal line to the stimulation actuation unit 30.

In addition, the signal pattern comparison unit 50 is adapted to compare the signal portion coming from the detector unit 20 to various comparison patterns from the signal pattern memory 52, and to associate it with the respectively most similar one of the comparison patterns. Depending on the comparison pattern with which the recorded signal portion is associated, the signal pattern comparison unit 50 forms an association signal which is also outputted to the stimulation actuation unit 30. From the difference signal from the difference value timer 36" and the association signal, which is characteristic of a typical signal pattern, from the signal pattern comparison unit 50, the stimulation actuation unit 30 forms a signal for actuating the controllable pulse generator 26. The stimulation intensity of a stimulation pulse which is delivered by the controllable pulse generator 26, in the case of the pacemaker shown in FIG. 2, therefore depends both on the time difference between the delivery of a stimulation pulse and the pick-up of a given signal feature, and also the characteristic form of that signal feature.

In addition, the pure time difference signal from the difference value timer 36" is fed directly to the backup stimulation unit 38 which triggers a backup stimulation pulse of the above-described kind if the time difference between the delivery of a stimulation pulse and the detection of a corresponding signal feature exceeds a predetermined limit value.

What is claimed is:

1. A stimulation apparatus, in particular for a human heart, comprising:
   a stimulation unit that is adapted to deliver a stimulation pulse having a pulse duration, a pulse strength and a stimulation intensity;
   a signal detector that is adapted to detect stimulation success based upon a picked-up signal;
   a control unit that is connected to the stimulation unit and to the signal detector and that is designed so that the stimulation intensity varies in dependence on the picked-up signal; and
   a time-determining unit that is at least indirectly connected to the control unit and with which a time difference between the delivery of the stimulation pulse and the pick-up of the picked-up signal or a signal feature of the picked-up signal can be detected, said picked-up signal or said signal feature indicating a stimulation success.

2. The stimulation apparatus of claim 1, wherein:
   at least one of the control unit and the stimulation unit is adapted to produce an increase in the stimulation intensity by prolonging the pulse duration or increasing the pulse strength and a reduction in the stimulation intensity by reducing the pulse duration or lowering the pulse strength.

3. The stimulation apparatus of claim 1, further comprising:
   an electrode that is connected to the stimulation unit and the signal detector and that is adapted to deliver the stimulation pulse and to pick up the signal.

4. The stimulation apparatus of claim 1, further comprising:

two electrodes that are spaced apart from each other and of which one is connected to the stimulation unit and the other is connected to the signal detector.

5. The stimulation apparatus of claim 1, wherein:

the control unit is adapted to produce a change in the stimulation intensity in dependence on the time difference.

6. The stimulation apparatus of claim 5, wherein:

the control unit is adapted to reduce the stimulation intensity if the time difference is shorter than a stored reference value.

7. The stimulation apparatus of claim 6, wherein:

the control unit is adapted for independently ascertaining the reference value or the predetermined morphological features by autocalibration.

8. The stimulation apparatus of claim 7, wherein:

the autocalibration is effected by detecting and comparing a plurality of time differences, in that the greatest time difference or the mean value of the longest time differences is determined from the plurality of the recorded time differences relative to the reference value.

9. The stimulation apparatus of claim 7, wherein:

the autocalibration is effected by determining that time difference which is associated with a stimulation pulse with the lowest level of stimulation intensity from a plurality of stimulation pulses.

10. The stimulation apparatus of claim 7, wherein:

the autocalibration is effected by determining the mean value of those time differences which are associated with a number of stimulation pulses with the lowest level of stimulation intensity from a plurality of stimulation pulses.

11. The stimulation apparatus of claim 7, wherein the autocalibration is effected by determining those morphological features which are associated with a stimulation pulse with the lowest level of stimulation intensity from a plurality of stimulation pulses.

12. The stimulation apparatus of claim 7, wherein:

the autocalibration is effected by determining mean values of those morphological features which are associated with a number of stimulation pulses with the lowest levels of stimulation intensity from a plurality of stimulation pulses.

13. The stimulation apparatus of claim 7, wherein:

the autocalibration is effected by determining mean values of those morphological features which are associated with a number of stimulation pulses with the lowest levels of stimulation intensity from a plurality of stimulation pulses.

14. The stimulation apparatus of claim 1, further comprising:

a morphology detector that is connected to the signal detector and the control unit and that is adapted to detect morphological features of the picked-up signal and to output a morphology signal to the control unit upon the occurrence of predetermined morphological features.

15. The stimulation apparatus of claim 14, wherein:

the morphology detector includes a signal shape memory; and a morphology comparison unit which is adapted to detect morphological features of the picked-up signal by comparing the picked-up signal with comparison signals from the signal shape memory.

16. The stimulation apparatus of claim 14, wherein:

the control unit is adapted to produce a change and preferably a reduction in the level of stimulation intensity in dependence on the morphology signal.

17. The stimulation apparatus of claim 14, wherein:

the control unit is adapted for independently ascertaining the reference value or the predetermined morphological features by autocalibration.

18. The stimulation apparatus of claim 17, wherein:

the autocalibration is effected by detecting and comparing a plurality of time differences, in that the greatest time difference or the mean value of the longest time differences is determined from the plurality of the recorded time differences relative to the reference value.

19. The stimulation apparatus of claim 17, wherein:

the autocalibration is effected by determining that time difference which is associated with a stimulation pulse with the lowest level of stimulation intensity from a plurality of stimulation pulses.

20. The stimulation apparatus of claim 17, wherein:

the autocalibration is effected by determining the mean value of those time differences which are associated with a number of stimulation pulses with the lowest levels of stimulation intensity from a plurality of stimulation pulses.

21. The stimulation apparatus of claim 17, wherein the autocalibration is effected by determining those morphological features which are associated with a stimulation pulse with the lowest level of stimulation intensity from a plurality of stimulation pulses.

22. The stimulation apparatus of claim 1, wherein the control unit is adapted, after the delivery of a stimulation pulse by the stimulation unit, to trigger the delivery of a second stimulation pulse of greater stimulation intensity if no picked-up signal or no signal feature of the picked-up signal is detected by the signal detector within a predetermined period of time after delivery of the first stimulation pulse.

23. The stimulation apparatus of claim 22, wherein:

the stimulation unit for the first and the second stimulation pulses includes a respective capacitor.

24. The stimulation apparatus of claim 1, wherein:

the stimulation apparatus is a cardiac pacemaker.

* * * * *